United States Patent [19]
McMillin

[11] Patent Number: 5,556,687
[45] Date of Patent: Sep. 17, 1996

[54] COMPOSITE STRUCTURE SUITABLE FOR USE AS A BONE PLATE AND METHOD FOR MAKING SAID STRUCTURE

[75] Inventor: Carl R. McMillin, Brecksville, Ohio

[73] Assignee: AcroMed Corporation, Cleveland, Ohio

[21] Appl. No.: 323,251

[22] Filed: Oct. 14, 1994

[51] Int. Cl.⁶ .............................. A61F 2/44; B32B 5/12; B32B 29/02; D04C 1/00
[52] U.S. Cl. ..................... 428/113; 156/148; 156/177; 156/182; 428/136; 428/257; 428/902; 623/17; 623/901; 87/8; 87/9
[58] Field of Search .......................... 428/36.1, 36.91, 428/113, 257, 902, 136; 156/148, 177, 182; 623/17, 901; 87/8, 9

[56] References Cited

U.S. PATENT DOCUMENTS

| | | | |
|---|---|---|---|
| 4,657,795 | 4/1987 | Foret | 428/36.1 |
| 4,696,290 | 9/1987 | Steffee . | |
| 4,743,260 | 5/1988 | Burton . | |
| 4,828,285 | 5/1989 | Foret et al. | 280/279 |
| 5,092,893 | 3/1992 | Smith . | |
| 5,143,669 | 9/1992 | Mott | 264/103 |
| 5,294,391 | 3/1994 | McMillin . | |

OTHER PUBLICATIONS

Composites, vol. 20., No. 6., Nov., 1989, Accelerated Testing Of A Composite Spine Plate, pp. 569–574.

*Primary Examiner*—James Withers
*Attorney, Agent, or Firm*—Tarolli, Sundheim, Covell, Tummino & Szabo

[57] ABSTRACT

A method of forming a composite structure comprises the steps of forming a radially inner portion of a preform with braided reinforcing fibers extending substantially transverse to an axis of the preform and forming a radially outer portion of the preform circumscribing the inner portion with braided reinforcing fibers extending substantially parallel to the axis of the preform. The preform is heated and consolidated in a mold into the composite structure. The composite structure has braided reinforcing fibers extending throughout a radially inner portion substantially transverse to an axis of the structure along which the structure is subject to splitting to resist splitting of the composite structure along the axis and braided reinforcing fibers extending throughout a radially outer portion substantially parallel to the axis to resist bending of the composite structure. The composite structure is particularly suitable for manufacturing a bone plate.

50 Claims, 4 Drawing Sheets

COMPOSITE STRUCTURE SUITABLE FOR USE AS A BONE PLATE AND METHOD FOR MAKING SAID STRUCTURE

BACKGROUND OF THE INVENTION

The present invention relates to a composite structure, and in particular relates to a composite structure comprising matrix material with braided reinforcing fibers and a method of making the structure.

There are many known composite structures which comprise a fiber reinforced matrix material. A known composite structure comprises a laminated stack of layers of matrix material containing linearly oriented reinforcing fibers. The direction of orientation of the reinforcing fibers in one layer may be at a different angle relative to the direction of orientation of the reinforcing fibers in an adjacent layer. A disadvantage of a laminated stack of layers of a matrix material containing linearly oriented reinforcing fibers is that there is no fiber reinforcement in a direction perpendicular to the layers. A known way to strengthen the structure in the direction perpendicular to the layers is to stitch the layers together. A disadvantage in stitching the layers together is that the stitching process is labor and equipment intensive. Also, known fiber reinforced composite structures are made from knitted fibers and woven fibers which form a three-dimensional structure. However, the making of these composite structures is also labor and equipment intensive.

SUMMARY OF THE INVENTION

In accordance with the present invention, a composite structure is made by a method which comprises the steps of braiding reinforcing fibers of a radially inner portion of a preform to extend substantially transverse to an axis of the preform along which the composite structure is subject to splitting. Reinforcing fibers of a radially outer portion circumscribing the radially inner portion are braided to extend substantially parallel to the axis of the preform. The preform is placed in a mold and heated to a temperature at which fibers which are to become the matrix material melt but the reinforcing fibers do not melt. The preform is consolidated in the mold. After heating and consolidating the preform, the composite structure is cooled so that a device such as a bone plate can be machined from the composite structure.

The composite structure comprises a radially inner portion of matrix material with braided reinforcing fibers extending throughout the inner portion substantially transverse to an axis of the composite structure along which the composite structure is subject to splitting to resist splitting of the composite structure. A radially outer portion of matrix material circumscribes the inner portion and has braided reinforcing fibers extending throughout the outer portion substantially parallel to the axis to resist bending of the composite structure.

The composite structure is similar to an I-beam in bending. The radially outer portions, like the outer webs of an I-beam, need the strength to resist bending of the composite structure because the stresses due to the bending are concentrated in the radially outer portions. The radially inner portion, like the connecting web of the I-beam, does not need to resist bending. The radially inner portion can be used to resist splitting of the composite structure.

The composite structure is machined into a bone plate for maintaining adjacent bone members, such as vertebrae or pieces of a broken bone, in a desired spatial relationship. When fasteners extend through openings in the bone plate to connect the bone plate to bone, the bone plate is subjected to clamping forces which could cause the bone plate to split along an axis. The braided reinforcing fibers in the radially inner portion of matrix material resist splitting of the bone plate due to the clamping forces applied to the bone plate by the fasteners. Furthermore, the braided reinforcing fibers extending through the radially outer portion resist bending of the bone plate and prevent movement between adjacent bone members which the bone plate is connected to.

A composite bone plate, as compared to a metal bone plate, is advantageous because it does not block the image of tissue on X-ray films and computerized tomography scans. A doctor can easily see if the pieces of a broken bone to which the composite bone plate is connected are healing properly or if adjacent vertebrae to which the composite bone plate is connected are fusing together properly. An X-ray marker, such as a titanium wire, may be braided into the composite bone plate so that a doctor may determine the position of the bone plate.

Another advantage of the composite bone plate is that the plate can be designed to prevent stress shielding. The stress-strain curve for bone has an initial region where some strain is achieved with very little stress. This initial region of the stress-strain curve is often called the "toe" of the stress-strain curve. At higher stresses, the curve becomes linear or proportional. The "toe" region allows for some deformation of the bone at low stress levels, while becoming more rigid at higher stresses, protecting against higher loads. The low stress deformation of bone is important in bone remodeling since the bone remodels to support applied loads.

When stiff metallic implants are connected to bone, the surrounding bone is shielded from applied stresses and the bone resorbs. If flexible implants are used, at high loads, the bone is deformed too much and damaged. The composite structure of the present invention is well suited for use as a bone plate since it can be made to have a stress-strain curve similar to that of bone, that is, with a low-stress "toe" region.

Contorted reinforcing fibers may be used in the composite structure to increase the size of the "toe" region. Twisted commingled yarn may be used in braiding the preform or the reinforcing fibers may be coiled, wavy, or kinked. With these structures, the matrix material of the bone plate deforms at low stress levels while the reinforcing fibers begin to straighten out. At higher stress levels, the reinforcing fibers straighten out to pick up the load and the composite plate becomes stiffer.

BRIEF DESCRIPTION OF THE DRAWINGS

The foregoing and other features of the present invention will become apparent to one skilled in the art upon consideration of the following description of the preferred embodiments of the invention with reference to the accompanying drawings, wherein.

DESCRIPTION OF THE PREFERRED EMBODIMENTS OF THE INVENTION

Figure 1:
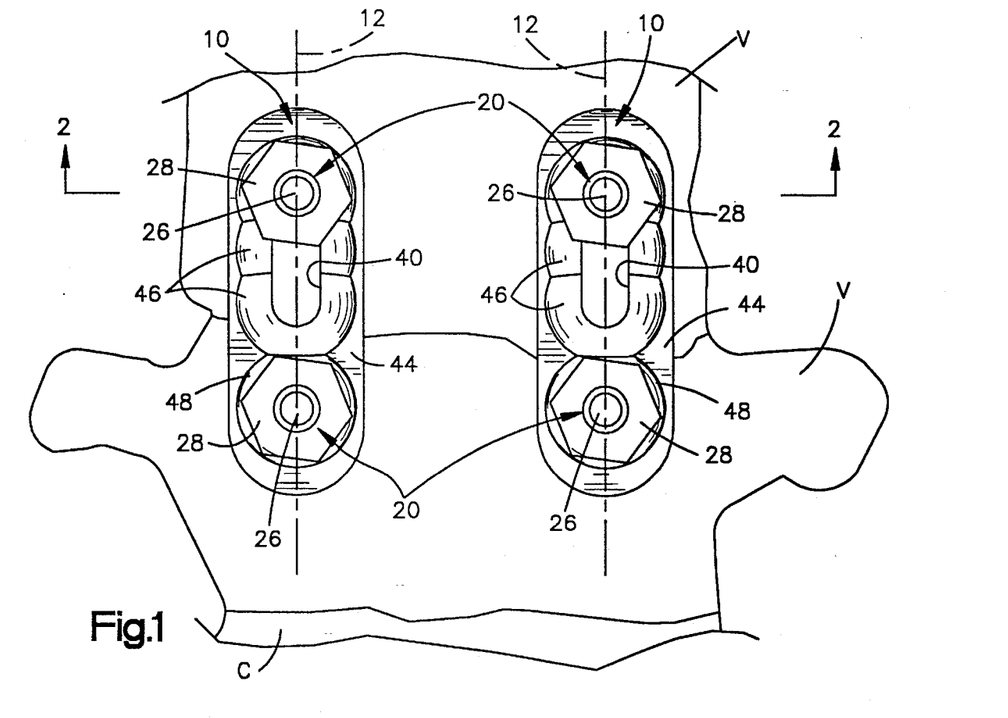
FIG. 1 is a fragmentary view of a portion of a spinal column on which a composite bone plate constructed in accordance with the present invention has been installed to maintain vertebrae in a desired spatial relationship.
Figure 2:
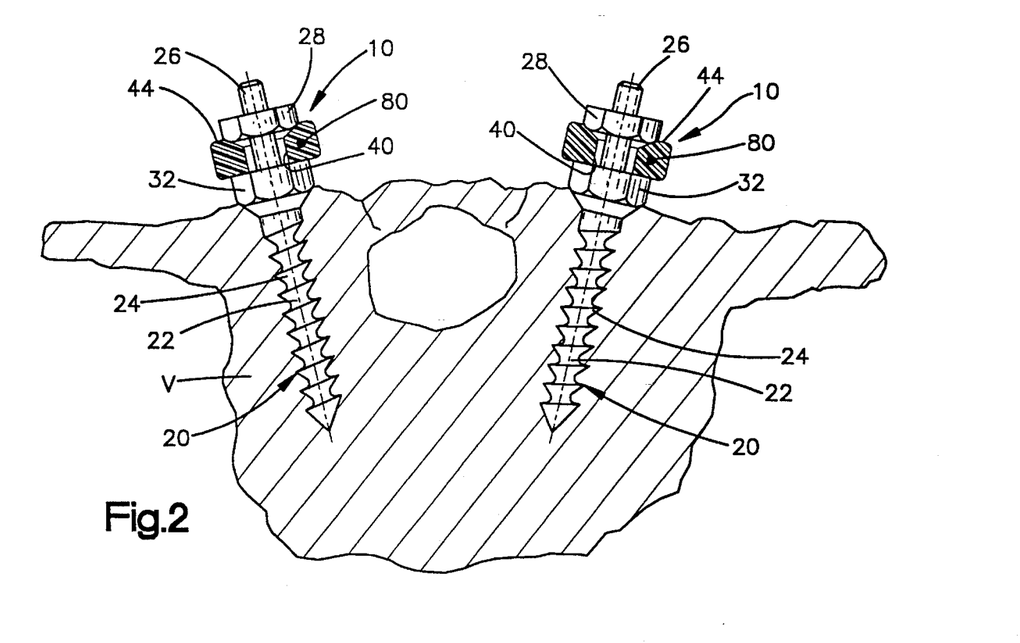
FIG. 2 is a sectional view, taken generally along the line 2—2 of FIG. 1, illustrating the manner in which fasteners are used to connect the composite bone plate with the vertebrae.
Figure 4:
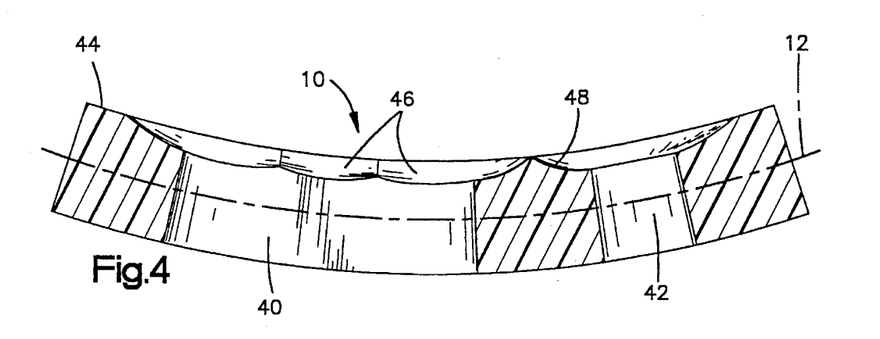
FIG. 4 is a sectional view of the composite bone plate of FIG. 3 taken along the line 4—4 of FIG. 3.

A pair of surgically implantable composite bone plates 10 (FIG. 1) for correcting deformation and/or degeneration of a spinal column C are connected with several vertebrae V of the spinal column by fasteners 20. Each composite bone plate 10 is elongate and has a rectangular cross-section taken in a plane extending perpendicular to a longitudinal central axis 12 of the plate (FIG. 2). Each composite plate 10 is preferably curved to conform to a desired curvature of the spinal column C, as illustrated in FIG. 4. The composite bone plates 10 have sufficient strength and rigidity to maintain the vertebrae V in the desired relationship. Although the composite bone plates are shown maintaining vertebrae in a desired spatial relationship, they may be used for maintaining pieces of a broken bone in a desired relationship.

The composite bone plates 10 are connected to respective vertebrae V by fasteners 20 (FIG. 2) made of a suitable biocompatible material, such as titanium or stainless steel. Each of the fasteners 20 has a threaded inner end portion 22 having a coarse helical thread convolution 24 which engages the vertebra V. An outer end portion 26 of the fastener 20 is provided with a relatively fine thread which engages an internal thread convolution on a clamp nut 28 preferably made of a suitable biocompatible material, such as titanium coated with titanium nitride. Wrenching flats (not shown) are provided on the outermost end of the outer end portion 26 of the fastener 20. Torque is applied to these wrenching flats to turn the relatively coarse helical thread convolution 24 into the vertebra V. Once the fastener 20 has been connected to the vertebra and the composite bone plate 10, the outer end portion of the fastener may be cut away to minimize the overall length of the fastener.

An intermediate portion 32 is provided with wrenching flats which can be engaged to hold the fastener 20 against rotation when the clamp nut 28 is tightened. In addition, the intermediate portion 32 of the fastener has a flat outer side surface which abuttingly engages the composite bone plate 10. When the clamp nut 28 is tightened, the composite bone plate 10 is securely gripped between the clamp nut 28 and the intermediate portion 32 of the fastener 20.

Although it is contemplated that the fastener 20 could have many different constructions, it is preferred to construct the fastener 20 in accordance with U.S. Pat. No. 4,854,311 which is assigned to the assignee of the present invention. Another possible fastener would include a piece with a plurality of ridges that mates with a plurality of ridges on the plate to prevent movement of the plate relative to the fastener.

Each of the composite bone plates 10 has a length which is at least sufficient to enable the bone plate to span at least two of the vertebrae V. In the embodiment of the invention illustrated in FIG. 1, the bone plates 10 span two vertebrae V. Of course, the length of the composite bone plates in any particular installation will depend upon the condition to be corrected and the number of vertebrae V to be held in a desired spatial relationship relative to each other by the composite bone plates. Preferably, each of the composite bone plates includes a titanium wire 80 (FIG. 2) extending along the longitudinal extent of the bone plate as an X-ray marker.

Figure 3:
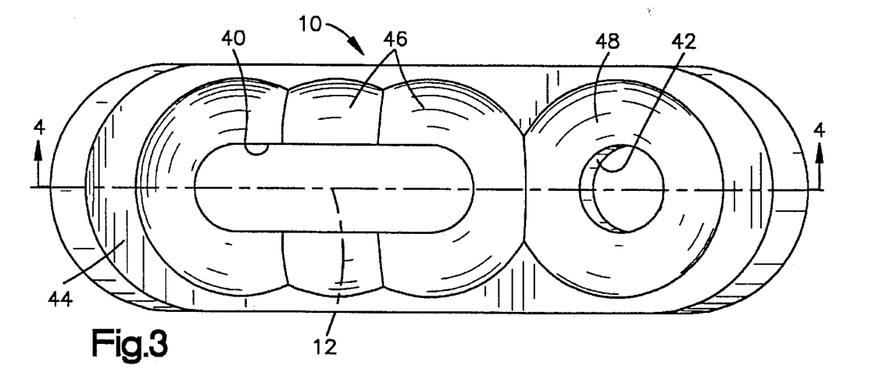
FIG. 3 is a plan view of the composite bone plate of FIG. 1.

Each of the composite bone plates 10 is identical and includes at least one slot 40 (FIGS. 3 and 4) and may include a circular opening 42 located adjacent an end portion of the bone plate. The bone plate 10 may have any number of slots for receiving fasteners depending on the length of the bone plate. The bone plate 10 has an upper surface 44 provided with spherical recesses 46 along the slot 40 defining a plurality of locations for receiving the fastener 20. If the bone plate 10 includes a circular opening 42, then upper surface 44 also includes a spherical recess 48 surrounding the opening 42 for receiving a fastener 20. The spherical recesses 46 and 48 have a radius that is the same as a radius of a spherical surface of the clamp nut 28 and is approximately 16 mm. The spherical recesses extend approximately 145° to help prevent splitting of the plate along the longitudinal axis 12 by directing most of the clamping forces applied to the plate in a direction normal to the surface 44 instead of transverse to the axis 12.

Preferably, a composite structure 60 from which the bone plate 10 is machined is formed by heating and consolidating a cylindrical braided preform 100 (FIG. 5) having a longitudinal axis 101. The preform 100 has a cross-section that forms a cross-section of a single composite structure 60 upon heating and consolidating the preform. The preform 100 may have any desired length to form one or a plurality of composite structures 60.

The preform 100 comprises a plurality of concentric layers of braided commingled yarn. The layers have varying braid angles with the inner layers having a large braid angle and the outer layers having a relatively small braid angle. The braid angle X is defined as half of the interlacing angle between yarns such as A and B, as shown in FIG. 6.

Preferably, the yarn is a commingled yarn known as Ultrapek/AS-4 Commingled Yarn manufactured by Cytec Inc., Anaheim, Calif. Ultrapek/AS-4 Commingled Yarn comprises Ultrapek polymer fibers made from poly(ether ketone ether ketone ketone) by BASF Inc., Charlotte, N.C. commingled with AS-4 carbon fibers made from a polyacrylonitrile percurser by Hercules Advanced Materials and Systems Company, Magna, Utah. The carbon fibers are the reinforcing fibers and the polymer fibers become matrix material when melted. Preferably, the reinforcing fibers are between 55% and 75% of the weight of the preform 100.

Alternatively, the material of which the yarn is made may be carbon fibers that have firmly adhering polymer powder bonded to the carbon fibers. Also, the material of which the yarn is made may be carbon fibers having a thin coating of polymer material. Also, the carbon fibers may be replaced with other carbon or graphite fibers or with glass fibers, silicon carbide fibers, or any other structural fibers. Also, the Ultrapek polymer may be replaced with other high performance and biocompatible polymers. These include, but are not limited to, other poly (aryl ether ketone)s such as PEEK, PEKK, and PEK, as well as poly (amide imide)s, poly (aryl sulfone)s, nylon, poly (butylene phthalate), poly (ethylene phthalate) and liquid crystal polymers or other similar polymers.

Figure 5:
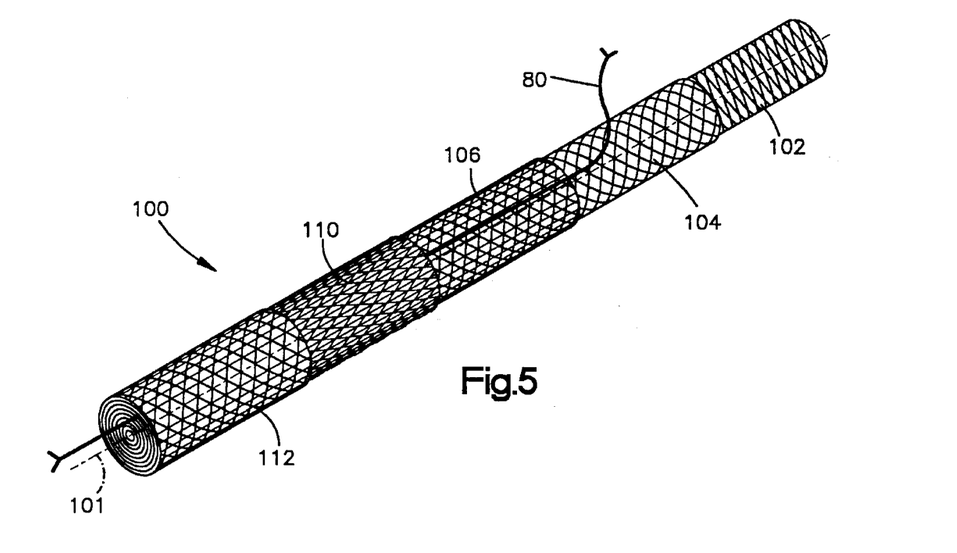
FIG. 5 is a schematic view of a preform, partially cut away to show various layers of the preform, used in forming the composite bone plate of FIG. 1.
Figure 6:
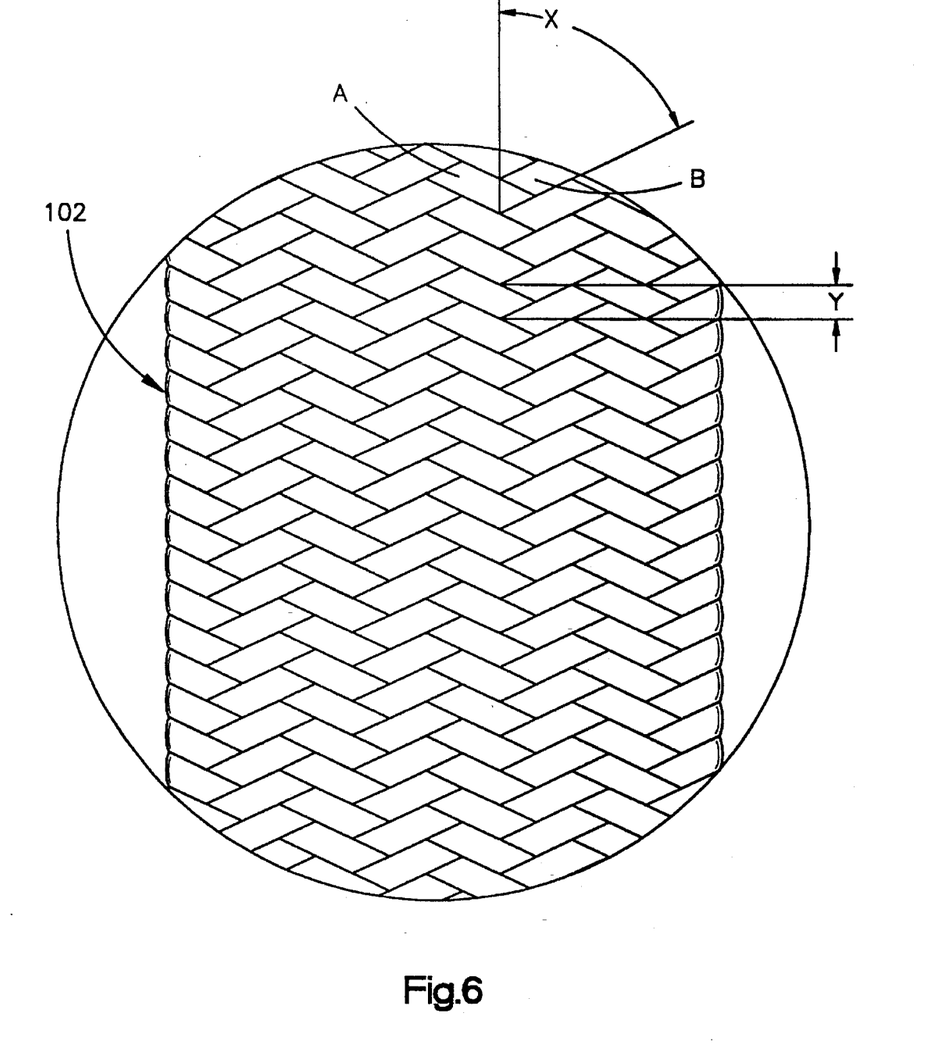
FIG. 6 is an enlarged plan view of a portion of a layer of the preform of FIG. 5.

The preform 100 includes a radially inner plurality of concentric layers 102, one of which is shown in FIGS. 5 and 6, of biaxially braided commingled yarn. The braid angle X of each of the layers 102 is between approximately 60° and 90°. It is desirable to have the braid angle as close to 90° as possible. Preferably, the inner plurality of concentric layers 102 comprises approximately one third of the thickness of the preform 100. The number of layers and the actual braid angle may vary depending on the braiding process.

An intermediate plurality of concentric layers 104 and 106 of braided yarn circumscribes the radially inner plurality of concentric layers 102. The braid angle of each of the layers of the intermediate plurality of concentric layers 104 and 106 is between approximately 40° and approximately 55°. The intermediate plurality of layers includes a first plurality of concentric layers 104, one of which is shown in FIG. 5, of biaxially braided yarn and a second plurality of concentric layers 106, one of which is shown in FIG. 5, of triaxially braided yarn circumscribing the first plurality of layers. Triaxially braided yarn has a pattern similar to the pattern of biaxially braided yarn shown in FIG. 6 with another system of yarn extending parallel to the longitudinal axis 101 of the preform 100 braided between the yarn extending transverse to the longitudinal axis.

The titanium wire 80 is braided into one of the second plurality of layers 106. Preferably, the intermediate plurality of layers 104 and 106 comprises approximately one third of the thickness of the preform 100. The actual number of intermediate layers 104 and 106 and the braid angle of the intermediate layers 104 and 106 may vary depending on the braiding process.

A radially outer plurality of concentric layers 110, one of which is shown in FIG. 5, of triaxially braided yarn circumscribes the intermediate plurality of layers 104 and 106. The braid angle of each of the layers of the outer plurality of concentric layers 110 is between approximately 0° and approximately 45°. It is desirable to have the braid angle as close to 0° as possible. Preferably, the outer plurality of concentric layers 110 comprises approximately one third of the thickness of the preform 100. The number of outer layers 110 and the actual braid angle of outer layers 110 may vary depending on the braiding process.

A radially outermost concentric layer 112 of triaxially braided yarn circumscribes the radially outer plurality of concentric layers 110. The outermost layer 112 has a braid angle of between approximately 40° and approximately 65°. The outermost layer 112 is tightly braided together so it does not come apart easily to provide for easy handling of the preform 100. Preferably, approximately half of the bias ends of the outermost layer 112 comprises a polymer yarn, the other half of the bias ends comprises Ultrapek/AS-4 commingled yarn and the axial ends comprise Ultrapek/AS-4 commingled yarn to provide a polymer rich surface of the composite structure 60.

Preferably, at least some of the reinforcing fibers are contorted prior to braiding the preform. The commingled yarn may be twisted, or coils, waves, or kinks may be formed in the reinforcing fibers. Therefore, the stress-strain curve (FIG. 7) of the composite structure has a "toe" region 200 and a linear region 202. At low stress levels the stress-strain curve is non-linear and at higher stress levels the stress and strain are approximately proportional. At low stresses the matrix material of the composite structure 60 deforms while the reinforcing fibers straighten out and at higher stresses the reinforcing fibers straighten and pick up the load.

EXAMPLES

Two examples of braided preforms from which composite bone plates have been formed are set forth below in Tables 1 and 2. The tables set out each concentric layer of the preform numbered from the radially innermost layer to the radially outermost layer. The braid angle and the picks per inch (ppi) for each layer are given in the tables. The picks per inch is defined as the distance between interlacing points and is labeled Y in FIG. 6.

TABLE 1

| Layer | Braid Angle (deg.) | ppi |
|---|---|---|
| 1 | 14 | 14 |
| 2 | 47 | 13 |
| 3 | 54 | 12 |
| 4 | 64 | 14 |
| 5 | 60 | 9 |
| 6 | 62 | 9 |
| 7 | 65 | 9 |
| 8 | 65 | 8 |
| 9 | 66 | 8 |
| 10 | 70 | 9 |
| 11 | 71 | 9 |
| 12 | 70 | 8 |
| 13 | 71 | 8 |
| 14 | 72 | 8 |
| 15 | 73 | 8 |
| 16 | 65 | 5 |
| 17 | 66 | 5 |
| 18 | 47 | 10 |
| 19 | 45 | 8 |
| 20 | 48 | 8.5 |
| 21 | 43 | 7 |
| 22 | 45 | 7 |
| 23 | 45 | 6.25 |
| 24 | 46 | 6.25 |
| 25 | 45 | 5.75 |
| 26 | 45 | 5.25 |
| 27 | 45 | 5 |
| 28 | 60 | 5 |

Layers 1–17 are biaxially braided with 4 bias ends. Layers 18–21 are biaxially braided with 16 bias ends. Layers 22 and 23 are triaxially braided with 16 bias ends and 16 axial ends. Layer 22 includes a bias end of titanium wire. Layers 24–27 are triaxially braided with 16 bias ends and 32 axial ends. Layer 28 is triaxially braided with 8 bias ends of commingled yarn, 24 bias ends of polymer yarn, and 48 axial ends of commingled yarn.

TABLE 2

| Layer | Braid Angle (deg.) | ppi |
|---|---|---|
| 1 | 33.4 | 14 |
| 2 | 50.8 | 13 |
| 3 | 65.5 | 14 |
| 4 | 71.4 | 14 |
| 5 | 72.2 | 12 |
| 6 | 74 | 12 |
| 7 | 75.8 | 12 |
| 8 | 77.8 | 12 |
| 9 | 59.1 | 4 |
| 10 | 60.1 | 4 |
| 11 | 54.7 | 4 |
| 12 | 44.1 | 2 |
| 13 | 44.8 | 2 |
| 14 | 45.1 | 8 |
| 15 | 26.6 | 3.5 |
| 16 | 25 | 3 |
| 17 | 26.6 | 3 |
| 18 | 30.1 | 3 |
| 19 | 22.2 | 2 |
| 20 | 28.8 | 2.5 |

TABLE 2-continued

| Layer | Braid Angle (deg.) | ppi |
| --- | --- | --- |
| 21 | 30.2 | 2.5 |
| 22 | 64.2 | 7 |

Layers 1–13 are biaxially braided with 4 bias ends. Layers 14 and 15 are triaxially braided with 16 bias ends and 16 axial ends. Layer 14 includes an axial end of titanium wire. Layers 16–21 are triaxially braided with 16 bias ends and 32 axial ends. Layer 22 is triaxially braided with 8 bias ends of commingled yarn, 8 bias ends of polymer yarn, and 48 axial ends of commingled yarn.

In both examples the first few radially innermost layers have braid angles from 14° to 54°. These braid angles are a result of the braiding process and machinery. It is preferred that these innermost layers have a braid angle as close to 90° as possible.

After the preform 100 is formed, it is heated and consolidated into an elongate composite structure 60 from which the bone plate 10 is machined. The preform 100 may be cut into a plurality of lengths to form a plurality of composite structures 60. The preform 100 is placed into a mold and the mold is placed into a high temperature consolidation press with vacuum capability. The vacuum chamber of the press is evacuated, the temperature is set to 800° F., and the pressure is set to 500 lbs. closing force. It requires approximately one hour for the press to reach 800° F. As the press displacement decreases, showing consolidation of the preform, the pressure is increased to 7,000 lbs. The temperature and pressure are maintained for 45 minutes and then the heat is turned off and the press cooling is turned on. After the mold has reached ambient temperature, the press is opened, the mold is removed, and the consolidated composite structure 60 is removed from the mold. The composite structure 60 is then machined to form a desired bone plate 10. After the bone plate 10 is machined it is placed in an ultrasonic bath with acetone to remove, any residual particulate debris.

The composite bone plate 10 is machined from the composite structure 60 (FIG. 7) comprising matrix material and reinforcing fibers. Preferably, the composite structure 60 is curved if the bone plate 10 is to be curved. The matrix material is the polymeric material, Ultrapek, and the reinforcing fibers are the AS-4 carbon fibers. Preferably, the reinforcing fibers make up between 55% and 75% of the weight of the composite structure 60.

Figure 7:
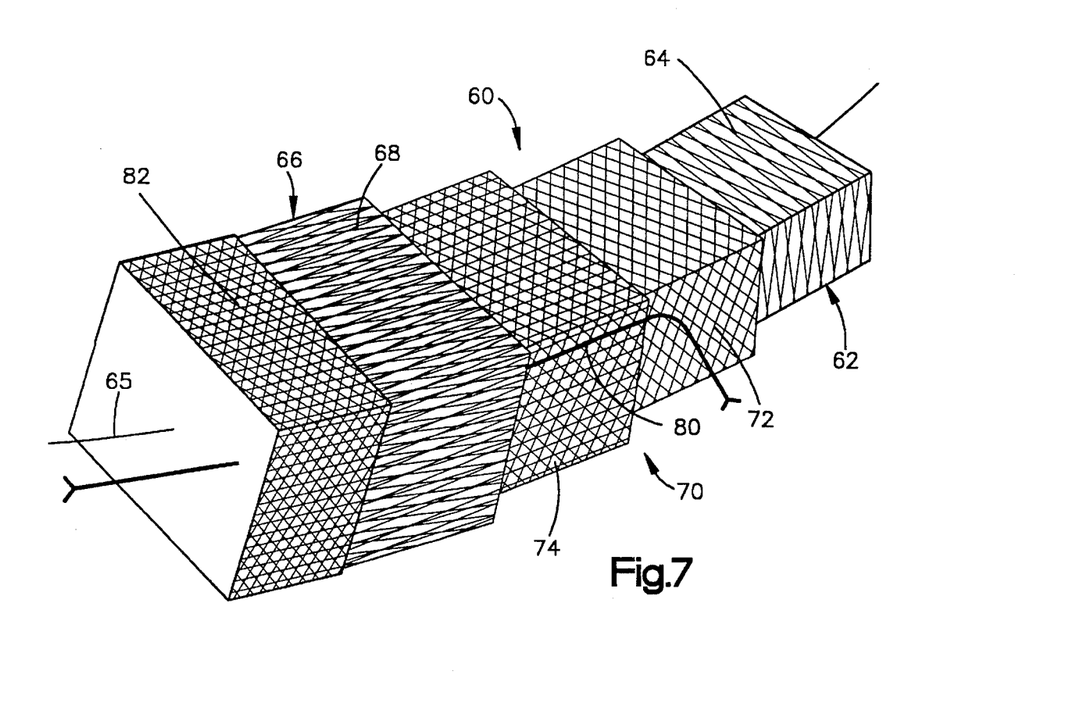
FIG. 7 is a schematic perspective view of a composite structure, partially cut away to show various portions of the structure, from which the bone plate of FIG. 1 is machined.
Figure 8:
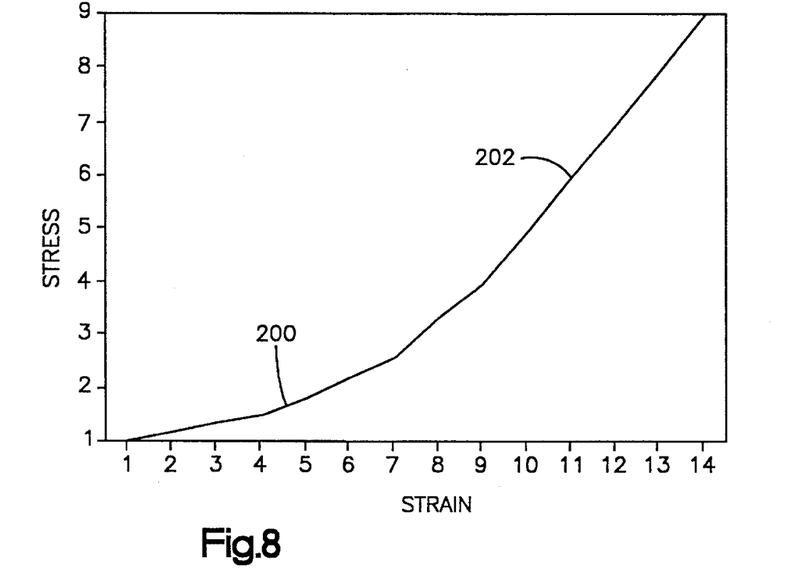
FIG. 8 is a graph showing the relationship between stress and strain for the composite structure of FIG. 7.

The composite structure 60 includes a radially inner portion of matrix material 62 with a plurality of concentric layers 64, one of which is shown in FIG. 7, of biaxially braided reinforcing fibers extending throughout the inner portion. The reinforcing fibers in the radially inner portion of matrix material 62 extend substantially transverse to a longitudinal axis 65 of the composite structure 60 to resist splitting of the structure along the longitudinal axis 65 when connected to bone as a bone plate. The axis 65 of the composite structure 60 becomes the axis 12 of the bone plate 10. The reinforcing fibers in the radially inner portion 62 have a braid angle between approximately 60° and 90°. It is desirable to have the braid angle as close to 90° as possible.

The composite structure 60 has a radially outer portion of matrix material 66 which circumscribes the radially inner portion of matrix material 62. A plurality of concentric layers 68, one of which is shown in FIG. 7, of triaxially braided reinforcing fibers extend throughout the radially outer portion of matrix material 66 substantially parallel to the longitudinal axis 65 to resist bending of the composite structure. The reinforcing fibers in the outer portion 66 have a braid angle between 0° and approximately 45°. It is desirable to have the braid angle as close to 0° as possible.

The composite structure 60 also includes an intermediate portion of matrix material 70 circumscribing the inner portion of matrix material 62 and circumscribed by the outer portion of matrix material 66. A plurality of concentric layers 72 and 74 of braided reinforcing fibers extend throughout the intermediate portion 70 and have a braid angle between approximately 40° and approximately 55°. A first plurality of concentric layers 72, one of which is shown in FIG. 7, of braided reinforcing fibers of the intermediate portion 70 are biaxially braided. A second plurality of concentric layers 74, one of which is shown in FIG. 7, of braided reinforcing fibers of the intermediate portion 70 circumscribes the first plurality of concentric layers 72 of the intermediate portion and are triaxially braided. The titanium wire 80 extends through the intermediate portion 70 and substantially parallel to the longitudinal axis 65 of the composite structure 60 to act as an X-ray marker.

The composite structure 60 has a radially outermost layer 82 of braided reinforcing fibers. The radially outermost layer 82 circumscribes the radially outer portion of matrix material 66. The radially outermost layer 82 is triaxially braided and has a braid angle between approximately 40° and approximately 60°.

From the above description of the invention, those skilled in the art will perceive improvements, changes and modifications. Such improvements, changes and modifications within the skill of the art are intended to be covered by the appended claims.

Having described the invention, the following is claimed:

1. A composite structure comprising:

a radially inner portion of matrix material;

a radially outer portion of matrix material circumscribing said inner portion;

braided reinforcing fibers extending throughout said inner portion substantially transverse to an axis along which said composite structure is subject to splitting to resist splitting of said composite structure along said axis; and braided reinforcing fibers extending throughout said outer portion substantially parallel to said axis to resist bending of said composite structure;

said directions of said reinforcing fibers resulting from heating and consolidating a preform made of matrix material and braided reinforcing fibers;

said composite structure including a plurality of openings for receiving fasteners.

2. A composite structure as set forth in claim 1 wherein said reinforcing fibers in said inner portion have a braid angle, which is half an interlacing angle between said reinforcing fibers in said intermediate portion, between approximately 60° and 90° and said reinforcing fibers in said outer portion have a braid angle, which is half an interlacing angle between said reinforcing fibers in said intermediate portion, between 0° and approximately 45°.

3. A composite structure as set forth in claim 2 further including an intermediate portion of matrix material circumscribed by said outer portion of matrix material and circumscribing said inner portion of matrix material and braided reinforcing fibers extending throughout said intermediate portion, said reinforcing fibers in said intermediate portion having a braid angle, which is half an interlacing angle between said reinforcing fibers in said intermediate portion, between approximately 40° and approximately 55°.

4. A composite structure as set forth in claim 3 wherein each of said inner, intermediate, and outer portions includes a plurality of concentric layers of braided reinforcing fibers.

5. A composite structure as set forth in claim 4 wherein said plurality of concentric layers of reinforcing fibers in said inner portion are biaxially braided.

6. A composite structure as set forth in claim 5 wherein said intermediate portion includes a first plurality of concentric layers of biaxially braided reinforcing fibers and a second plurality of concentric layers of triaxially braided reinforcing fibers, said second plurality of concentric layers of reinforcing fibers circumscribing said first plurality of concentric layers of reinforcing fibers in said intermediate portion.

7. A composite structure as set forth in claim 6 wherein said plurality of concentric layers of reinforcing fibers in said outer portion are triaxially braided.

8. A composite structure as set forth in claim 3 further including a titanium wire extending through said intermediate portion.

9. A composite structure as set forth in claim 2 further including a radially outermost portion circumscribing said outer portion, said outermost portion including braided reinforcing fibers with a braid angle, which is half an interlacing angle between said reinforcing fibers in said intermediate portion, between approximately 40° and approximately 65°.

10. A composite structure as set forth in claim 11 wherein said openings are defined by spherical recesses in a side surface of said composite structure which define a plurality of locations for receiving fasteners, each of said recesses defining a spherical arc extending approximately 145°.

11. A composite structure as set forth in claim 10 wherein at least one of said openings is a slot, said recesses defining a plurality of locations along said slot for receiving fasteners.

12. A composite structure as set forth in claim 11 further including a round opening located at an axial end portion of said structure.

13. A composite structure as set forth in claim 1 wherein said reinforcing fibers are between 55% and 75% of the weight of said composite structure.

14. A composite structure as set forth in claim 1 wherein at least some of said reinforcing fibers are contorted.

15. A composite structure as set forth in claim 14 wherein said at least some of said reinforcing fibers are coiled.

16. A composite structure as set forth in claim 14 wherein said at least some of said reinforcing fibers are twisted.

17. A method of forming a composite structure which in use is subject to splitting along an axis and bending, said method comprising the steps of:

providing a radially inner portion of a perform with a first plurality of braided reinforcing fibers extending substantially transverse to the axis;

providing a radially outer portion of the preform circumscribing the inner portion with a second plurality of braided reinforcing fibers extending substantially parallel to the axis;

heating and consolidating the preform to form a matrix with the first and second plurality of braided reinforcing fibers extending through inner and outer portions of the matrix material, respectively; and forming a plurality of openings in the composite structure for receiving fasteners.

18. A method as set forth in claim 17 including braiding the first plurality of reinforcing fibers of the inner portion of the preform with a braid angle, which is half an interlacing angle between said reinforcing fibers in said inner portion, between approximately 60° and 90° and braiding the second plurality of reinforcing fibers of the outer portion with a braid angle, which is half an interlacing angle between said reinforcing fibers in said outer portion, between 0° and approximately 45°.

19. A method as set forth in claim 18 including providing an intermediate portion of the preform circumscribed by the outer portion and circumscribing the inner portion with a third plurality of braided reinforcing fibers having a braid angle, which is half an interlacing angle between said reinforcing fibers in said intermediate portion, between approximately 40° and approximately 55°.

20. A method as set forth in claim 19 including providing a radially outermost portion of the preform circumscribing the outer portion with braided reinforcing fibers having a braid angle, which is half an interlacing angle between said reinforcing fibers in said intermost portion, between approximately 40° and approximately 65°.

21. A method as set forth in claim 20 including braiding approximately 50% of bias ends of the radially outermost portion with matrix yarn, approximately 50% of the bias ends of the radially outermost portion with commingled matrix and reinforcing fiber yarn, and axial ends of the radially outermost portion with commingled matrix and reinforcing fiber yarn.

22. A method as set forth in claim 19 including forming each of the inner, intermediate, and outer portions to be approximately one third the thickness of the preform.

23. A method as set forth in claim 19 including forming each of the inner, intermediate, and outer portions out of a plurality of concentric layers of braided fibers.

24. A method as set forth in claim 23 including biaxially braiding the plurality of concentric layers of the inner portion.

25. A method as set forth in claim 23 including biaxially braiding a first plurality of concentric layers of the intermediate portion and triaxially braiding a second plurality of concentric layers of the intermediate portion circumscribing the first plurality of concentric layers of the intermediate portion.

26. A method as set forth in claim 23 including triaxially braiding the plurality of concentric layers of the outer portion.

27. A method as set forth in claim 23 including braiding a titanium wire into the intermediate portion.

28. A method as set forth in claim 17 including contorting at least some of the reinforcing fibers prior to braiding.

29. A method as set forth in claim 28 wherein said step of contorting the reinforcing fibers includes forming coils in the reinforcing fibers.

30. A method as set forth in claim 28 including forming the preform with commingled yarn.

31. A method as set forth in claim 30 wherein the step of contorting the reinforcing fibers includes twisting the commingled yarn.

32. A method as set forth in claim 17 including forming spherical recesses extending approximately 145° in a side surface of the composite structure to define a plurality of locations for receiving fasteners.

33. A method as set forth in claim 32 including forming a slot with at least two recesses defining locations for receiving fasteners.

34. A method as set forth in claim 33 including forming a round opening at an axial end portion of the composite structure for receiving one fastener.

35. A method as set forth in claim 17 further including forming the composite structure with the reinforcing fibers making up between 55% and 75% of the weight of the composite structure.

36. A composite bone plate for retaining bone portions in a desired spatial relationship, said bone plate comprising:

first surface means for facing the bone portions;

second surface means for facing away from the bone portions extending generally parallel to said first surface means;

third surface means for defining a longitudinally extending slot extending through said bone plate for receiving a fastener to connect said bone plate to one of the bone portions;

a radially inner portion of matrix material;

a radially outer portion of matrix material circumscribing said inner portion;

braided reinforcing fibers extending throughout said inner portion substantially transverse to a longitudinal axis of said slot along which said bone plate is subject to splitting to resist splitting of said bone plate along said longitudinal axis; and braided reinforcing fibers extending throughout said outer portion substantially parallel to said longitudinal axis of said slot to resist bending of said bone plate;

said directions of said reinforcing fibers resulting from heating and consolidating a preform made of matrix material and braided reinforcing fibers.

37. A composite bone plate as set forth in claim 36 wherein said reinforcing fibers in said inner portion have a braid angle, which is half an interlacing angle between said reinforcing fibers in said outermost portion, between approximately 60° and 90° and said reinforcing fibers in said outer portion have a braid angle, which is half an interlacing angle between said reinforcing fibers in said outer portion, between 0° and approximately 45°.

38. A composite bone plate as set forth in claim 37 further including an intermediate portion of matrix material circumscribed by said outer portion of matrix material and circumscribing said inner portion of matrix material and braided reinforcing fibers extending throughout said intermediate portion, said reinforcing fibers in said intermediate portion having a braid angle, which is half an interlacing angle between said reinforcing fibers in said intermediate portion, between approximately 40° and approximately 55°.

39. A composite bone plate as set forth in claim 38 wherein each of said inner, intermediate, and outer portions includes a plurality of concentric layers of braided reinforcing fibers.

40. A composite bone plate as set forth in claim 39 wherein said plurality of concentric layers of reinforcing fibers in said inner portion are biaxially braided.

41. A composite bone plate as set forth in claim 40 wherein said intermediate portion includes a first plurality of concentric layers of biaxially braided reinforcing fibers and a second plurality of concentric layers of triaxially braided reinforcing fibers, said second plurality of concentric layers of reinforcing fibers circumscribing said first plurality of concentric layers of reinforcing fibers in said intermediate portion.

42. A composite bone plate as set forth in claim 41 wherein said plurality of concentric layers of reinforcing fibers in said outer portion are triaxially braided.

43. A composite bone plate as set forth in claim 38 further including a titanium wire extending through said intermediate portion.

44. A composite bone plate as set forth in claim 39 further including a radially outermost portion circumscribing said outer portion, said outermost portion including braided reinforcing fibers with a braid angle, which is half an interlacing angle between said reinforcing fibers in said outermost portion, between approximately 40° and approximately 65°.

45. A composite bone plate as set forth in claim 36 wherein said third surface means includes spherical recesses in said first surface means of said composite bone plate which define a plurality of locations for receiving fasteners, each of said recesses defining a spherical arc extending approximately 145°.

46. A composite bone plate as set forth in claim 45 further including a round opening located at an axial end portion of said bone plate.

47. A composite bone plate as set forth in claim 36 wherein said reinforcing fibers are between 55% and 75% of the weight of said bone plate.

48. A composite bone plate as set forth in claim 36 wherein at least some of said reinforcing fibers are contorted.

49. A composite bone plate as set forth in claim 48 wherein said at least some of said reinforcing fibers are coiled.

50. A composite bone plate as set forth in claim 48 wherein said at least some of said reinforcing fibers are twisted.

* * * * *